United States Patent [19]

Tamm

[11] Patent Number: 4,598,700
[45] Date of Patent: Jul. 8, 1986

[54] APPARATUS FOR MEASURING PULSE RATE AND PULMONARY VOLUME

[76] Inventor: Ulf S. Tamm, 122 Ch. de la Montagne, 1224 Chene Bougeries, Switzerland

[21] Appl. No.: 699,232

[22] Filed: Feb. 8, 1985

Related U.S. Application Data

[63] Continuation of Ser. No. 475,217, Mar. 14, 1983, abandoned.

[51] Int. Cl.⁴ .............................................. A61B 5/08
[52] U.S. Cl. ................... 128/671; 128/689; 128/726
[58] Field of Search ............... 128/670, 671, 689, 690, 128/725, 726

[56] References Cited

U.S. PATENT DOCUMENTS

| | | | |
|---|---|---|---|
| 3,675,640 | 7/1972 | Gatts | 128/671 |
| 3,922,525 | 11/1975 | Kozak et al. | 128/725 |
| 3,962,917 | 6/1976 | Terada | 128/725 |
| 4,036,211 | 7/1977 | Veth et al. | 128/671 |
| 4,120,296 | 10/1978 | Prinz | 128/690 |
| 4,121,574 | 10/1978 | Lester | 128/689 |
| 4,125,111 | 11/1978 | Hudspeth et al. | 128/689 |
| 4,305,401 | 12/1981 | Reissmueller et al. | 128/690 |
| 4,334,544 | 6/1982 | Hill et al. | 128/687 |
| 4,353,152 | 10/1982 | O'Connor et al. | 128/689 |
| 4,356,825 | 11/1982 | Veth | 128/671 |
| 4,407,295 | 10/1983 | Stever et al. | 128/670 |
| 4,441,505 | 4/1984 | Edwards et al. | 128/726 |

OTHER PUBLICATIONS

Iton et al, "Non-Invasive Respiratory Function Monitoring System," Proceedings of the Vth ICEBI, Aug. 1981, pp. 341-344.

Primary Examiner—Kyle L. Howell
Assistant Examiner—Ruth S. Smith
Attorney, Agent, or Firm—Vorys, Sater, Seymour and Pease

[57] ABSTRACT

A portable apparatus which enables the user to measure his pulse rate and pulmonary volume during exercise comprises a single case equipped with a neck cord and comprising all of the elements necessary for taking such measurements, i.e., a mouth-piece into which to exhale, a switch, an electro-optical display, means for measuring the volume of exhaled air, pulse sensing means, electronic circuits and batteries.

15 Claims, 6 Drawing Figures

APPARATUS FOR MEASURING PULSE RATE AND PULMONARY VOLUME

This application is a continuation of application Ser. No. 475,217, filed Mar. 14, 1983, abandoned.

BACKGROUND OF THE INVENTION

1. Field of the Invention

This invention relates to apparatus for measuring pulse rate and pulmonary volume, and more particularly to portable apparatus for measuring pulse rate and vital capacitry during exercise.

2. Brief Description of the Prior Art

In recent decades, extensive public education campaigns have made people in the industrialized world aware of the importance of exercise in fighting cardiovascular disease. Such campaigns, coinciding with general improvements in living conditions, have made possible the very rapid spread of sports such as skiing, tennis, and jogging. An increasing number of individuals involved in such sports have shown an interest in being able to take regular measurements of the physiological parameters which will allow them to check on the proper functioning of their bodies.

From the medical point of view, a considerable number of measurements of physiological functions are necessary for precise overall diagnosis of the state of health and conditioning of an athlete. Lacking the necessary knowledge, a layman can neither take nor interpret most of these measurements. However, there are certain basic measurements that the layman can use to check his own physical condition by comparing the measurements he takes to known average values. These measures are primarily: blood pressure, pulse rate at rest or during physical exertion, pulse recovery time after physical exertion, and effective pulmonary volume, i.e., the volume of that part of the lungs used to exchange respiratory gases. The effective pulmonary volume is also known as the vital capacity, i.e., the total lung volume less the residual volume or volume remaining after a complete or maximal expiration. Mechanical and electronic instruments for taking separate measurements of these functions are known. There are also electronic instruments for measuring blood pressure and pulse rate. Instruments designed for measuring pulmonary volume are generally bulky and can not be used with comfort by the individual during athletic activity. Sports medicine recognizes the value of regular and repeated measurements of blood pressure and pulse (cardiac functions), as well as of pulmonary functioning. Measurements of these physiological functions during and/or immediately following sustained athletic activity is also of great value in the determination of the athlete's state of conditioning.

Therefore, a need has continued to exist for a simple and portable apparatus which will provide the athlete with measurements of pulse rate and vital capacity during exercise.

SUMMARY OF THE INVENTION

Accordingly, it is an object of the present invention to offer the athlete the possibility of taking regular measurements of his pulse and vital capacity by means of an instrument designed so that it can be easily taken along during athletics, enabling measurements to be taken even at moments of peak exertion.

A further object of the invention is to provide a portable apparatus for measuring pulse rate.

A further object is to provide a portable apparatus for measuring vital capacity.

A further object is to provide a portable apparatus for measuring both pulse rate and respiratory volume during exercise.

Further objects of the invention will become apparent from the description which follows.

The objects of the invention are attained by an apparatus for measuring pulse rate and respiratory volume comprising means for measuring pulse rate, means for measuring vital capacity, and a case containing both of the measuring means, the case being small enough to be conveniently carried during athletic activity.

BRIEF DESCRIPTION OF THE DRAWINGS

The invention will be more easily understood by reference to the accompanying drawings wherein.

DETAILED DESCRIPTION OF THE INVENTION AND PREFERRED EMBODIMENTS

Figure 1:
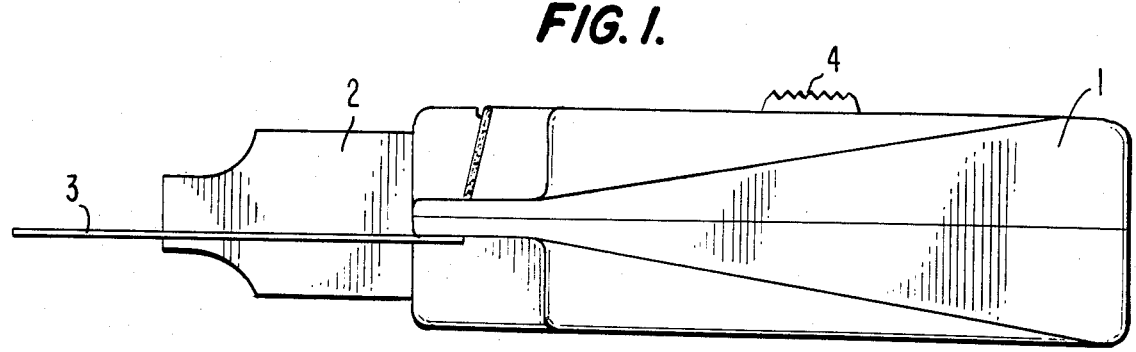
FIG. 1 is a side elevational view of the apparatus.
Figure 2:
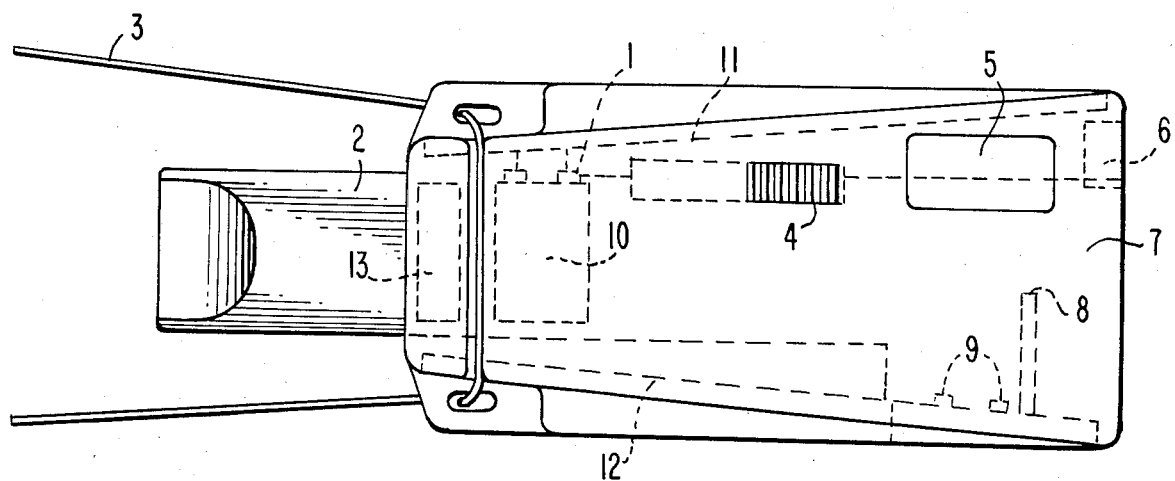
FIG. 2 is a plan view of the apparatus.
Figure 3:
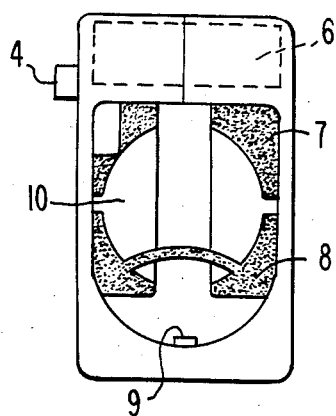
FIG. 3 is a view of the apparatus taken along line 3—3 of FIG. 2.

The illustrated apparatus comprises a metal or plastic case 1, fitted with a removable mouth-piece 2. The case is equipped with a cord 3 enabling the device to be worn around the neck. Alternatively, the case may be provided with means for fastening the apparatus to a limb of the user or to the user's clothing. The upper part of the case contains a switch 4 for preselecting the various functions of the device. The case also contains electro-optical display means 5. While any display means capable of being actuated by an electrical signal may be used, it is preferred, for reasons of compactness and light weight, that the display device be an electro-optical display device, e.g., an array of light emitting diodes or a liquid crystal display. Conveniently, the display is a multi-segment display capable of displaying one or more numerals, e.g., one or more conventional 7-segment digital electro-optical displays. The case has a space 6 for the batteries that supply power for the electronic circuits. The case is traversed from end to end by a passage 7. The lower part of passage 7 contains a spring 8 and opto-electronic means 9 for sensing the pulse rate. The upper part of passage 7 comprises a turbine 10 and a filter 13. Inside the case are spaces for two electronic circuits 11 and 12.

Figure 4:
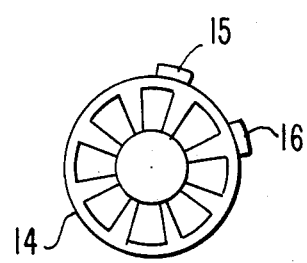
FIG. 4 is a schematic representation of a turbine forming part of the means for measuring vital capacity.

The turbine illustrated in FIG. 4 consists of a light plastic impeller 14 and opto-electronic sensing means 15 and 16.

Figure 5:
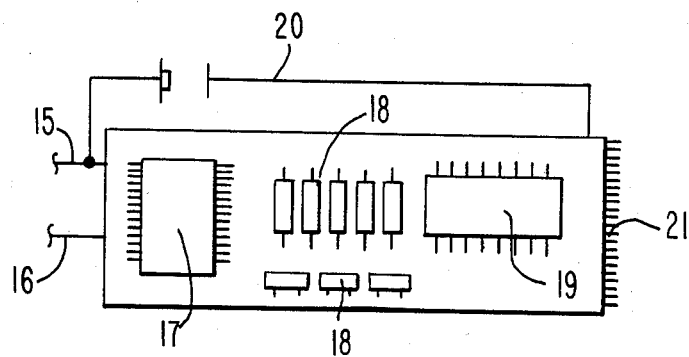
FIG. 5 is a pictorial representation of the electronic circuit for the vital capacity measurement function.

Electronic circuit 11 illustrated in FIG. 5 consists of an integrated circuit 17, passive components 18, and an integrated decoding circuit 19 to decode the signal and drive the digital display.

Figure 6:
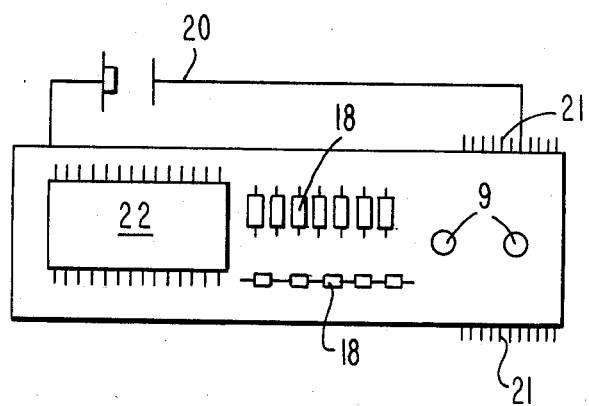
FIG. 6 is a pictorial representation of the electronic circuit for the pulse measurement means of the apparatus.

Electronic circuit 12 illustrated in FIG. 6 consists of a commercially available micro-processor 22 for processing the pulse rate signals, passive components 18, and space for opto-electonic pulse sensing means 9.

The two circuits are supplied by three 1.5 volt batteries represented schematically by numeral 20. The electronic circuits are equipped with terminals 21. Because nearly all of its elements are combined in a single case, the device is particularly simple to use, so that a brief description of its method of use, either written or graphically represented on case 1, (e.g., immediately below switch 4), is all that is needed to enable anyone to use the device correctly.

The device is used as follows:

To measure lung volume:

The medical measurement made by the device is the vital capacity, i.e., pulmonary volume, excluding residual volume. In a different embodiment, through modification of the electronic circuit, the medical measurement may be $FEV_1$, i.e., the volume of air expired in one second.

To measure vital capacity, the user exhales completely into mouth-piece 2. The exhaled air enters passage 7, through filter 13 and turbine 10, causing turbine impeller 14 to turn. One of the blades of impeller 14 is colored so as to produce a signal in opto-electronic means 15-16, which consist of a light-emitting diode (LED), e.g., an infrared light transmitter 15, and a light-sensitive receiver, e.g., an infrared-sensitive receiver 16. A digital signal is thus generated for each revolution of turbine impeller 14. This signal is transmitted to integrated circuit 17, a counting circuit which accumulates the count of revolutions of the turbine.

The total count of integrated circuit 17 is multiplied by a constant such that the displayed result of the total revolution count equals the volume in liters of air exhaled.

Thus processed and decoded, the signal is displayed in liters on opto-electronic digital display 5.

To measure pulse rate:

A finger is inserted into the lower part of passage 7 and held by spring 8 so that the fingertip presses lightly against opto-elctronic sensor 9, consisting of an infrared light transmitter and infrared receiver. The variation of the volume of blood in the capillaries of the finger is sufficient to produce a digital signal in elctro-optical sensor 9. The signal is transmitted to microprocessor 22 which computes the pulse rate (number of pulses per minute), and transmits the result to the electro-optical display.

To preselect the desired measurement, switch 4 is equipped with the necessary number of positions.

Having now fully described the invention, it will be apparent to one skilled in the art that many variations and modifications can be made without departing from the teaching and spirit thereof.

What is claimed as new and sought to be protected by Letters Patent of the United States is:

1. A portable apparatus for measuring pulse rate and vital capacity of a person, comprising:
    a case having means formed therein for transmitting expired air therethrough and for receiving a portion of a person's body to measure pulse rate;
    means for measuring vital capacity disposed within said means for transmitting expired air and for receiving a portion of a person's body;
    means for measuring pulse rate disposed within said means for transmitting expired air and for receiving a portion of a person's body; and
    a source of electrical power disposed within said case for operating said means for measuring vital capacity and for operating said means for measuring pulse rate.

2. The apparatus of claim 1 wherein said means for measuring vital capacity comprises a turbine disposed in said transmitting means such that said turbine is driven into rotation by the expired air.

3. The apparatus of claim 2, wherein said means for measuring vital capacity further comprises means for sensing the rotation of said turbine.

4. The apparatus of claim 3, wherein said means for measuring vital capacity further comprises means for counting the revolutions of said turbine during at least one complete expiration.

5. The apparatus of claim 4 wherein said means for measuring vital capacity further comprises means for converting the number of revolutions of said turbine into a value representing vital capacity.

6. The apparatus of claim 3 wherein said turbine comprises at least one blade, and wherein said means for sensing the rotation of said turbine comprises optical means for detecting passage of said blade past said optical means.

7. The apparatus of claim 6 wherein said optical means comprises a light-emitting diode and a light-sensitive detector.

8. The apparatus of claim 1, further comprising display means disposed within said case for displaying pulse rate and for displaying vital capacity.

9. The apparatus of claim 8, further comprising switch means connected to said display means for selecting a display of either pulse rate or vital capacity.

10. The apparatus of claim 8 wherein said display means comprises electro-optical display means.

11. The apparatus of claim 9 wherein said display means comprises a single display means.

12. The apparatus of claim 8, wherein said means for measuring pulse rate comprises means for sensing the periodic variation of blood volume in a finger, means for counting said periodic variations, whereby a pulse count is obtained, and means for converting said pulse count into a pulse rate and displaying said pulse rate on said display means.

13. The apparatus of claim 12 further comprising means disposed within said receiving means for holding a finger in contact with said means for sensing the variation of blood volume in said finger.

14. The apparatus of claim 12 wherein said means for sensing the variation of blood volume comprises an infrared light-emitting diode and an infrared-sensitive receiver.

15. The apparatus of claim 13 wherein said means for holding a finger comprises spring means.

* * * * *